US012594092B2

(12) United States Patent
Massimini et al.

(10) Patent No.: US 12,594,092 B2
(45) Date of Patent: Apr. 7, 2026

(54) FLY BY WIRE CONTROL FOR ATHERECTOMY

(71) Applicant: Boston Scientific Scimed, Inc., Maple Grove, MN (US)

(72) Inventors: Daniel Frank Massimini, Brooklyn Park, MN (US); Michael Kaland, Minneapolis, MN (US); Corydon Carlson, Stillwater, MN (US); Jarrod Kenneth Neuharth, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 612 days.

(21) Appl. No.: 17/894,059

(22) Filed: Aug. 23, 2022

(65) Prior Publication Data

US 2023/0123902 A1 Apr. 20, 2023

Related U.S. Application Data

(60) Provisional application No. 63/257,681, filed on Oct. 20, 2021.

(51) Int. Cl.
*A61B 17/3207* (2006.01)
*A61B 34/00* (2016.01)
(Continued)

(52) U.S. Cl.
CPC ...... *A61B 17/320758* (2013.01); *A61B 34/25* (2016.02); *A61B 34/76* (2016.02);
(Continued)

(58) Field of Classification Search
CPC . A61B 17/320758; A61B 34/25; A61B 34/76; A61B 34/30; A61B 2017/320004; A61B 17/3207
See application file for complete search history.

(56) References Cited

U.S. PATENT DOCUMENTS

| | | | |
|---|---|---|---|
| 62,123 | A | 2/1867 | Elgin |
| 2,088,654 | A | 8/1937 | Hull |

(Continued)

FOREIGN PATENT DOCUMENTS

| | | |
|---|---|---|
| CA | 2682488 A1 | 10/2008 |
| DE | 202005022017 U1 | 5/2012 |

(Continued)

OTHER PUBLICATIONS

International Search Report and Written Opinion dated Aug. 20, 2019 for International Application No. PCT/US2019/033748.
(Continued)

*Primary Examiner* — Brigid K Byrd
(74) *Attorney, Agent, or Firm* — Seager, Tufte & Wickhem, LLP

(57) ABSTRACT

An atherectomy system includes a user interface that an operator engages with in order to indicate requested movement of a drive assembly. One or more sensors are adapted to ascertain one or more conditions of the drive assembly and to output one or more condition signals to a controller that is operably coupled with the operator assembly and the drive assembly. The controller is adapted to receive the request signal from the operator assembly and the one or more condition signals, to determine a command signal in response to the received request signal and the received one or more condition signals, and provide the command signal to the drive assembly. The drive assembly is adapted to move relative to the advancer assembly in accordance with the command signal.

20 Claims, 7 Drawing Sheets

(51) Int. Cl.
    *A61B 17/00*       (2006.01)
    *A61B 17/32*       (2006.01)
    *A61B 90/00*       (2016.01)

(52) U.S. Cl.
    CPC ............... *A61B 2017/00199* (2013.01); *A61B 2017/00221* (2013.01); *A61B 2017/00398* (2013.01); *A61B 2017/320004* (2013.01); *A61B 2090/064* (2016.02)

(56)           References Cited

U.S. PATENT DOCUMENTS

| | | |
|---|---|---|
| 3,913,196 A | 10/1975 | Maday |
| 4,395,167 A | 7/1983 | Maternus |
| 4,507,028 A | 3/1985 | Matsushita |
| 4,679,557 A | 7/1987 | Opie et al. |
| 5,116,350 A | 5/1992 | Stevens |
| 5,287,858 A | 2/1994 | Hammerslag et al. |
| 5,308,354 A | 5/1994 | Zacca et al. |
| 5,314,407 A | 5/1994 | Auth et al. |
| 5,417,703 A | 5/1995 | Brown et al. |
| 5,478,344 A | 12/1995 | Stone et al. |
| 5,501,694 A | 3/1996 | Ressemann et al. |
| 5,540,707 A | 7/1996 | Ressemann et al. |
| 5,563,481 A | 10/1996 | Krause |
| 5,572,609 A | 11/1996 | Li |
| 5,626,444 A | 5/1997 | Campian |
| 5,632,755 A | 5/1997 | Nordgren et al. |
| 5,674,235 A | 10/1997 | Parisi |
| 5,681,336 A | 10/1997 | Clement et al. |
| 5,709,661 A | 1/1998 | Van Egmond et al. |
| 5,766,192 A | 6/1998 | Zacca |
| 5,779,722 A | 7/1998 | Shturman et al. |
| 5,823,990 A | 10/1998 | Henley |
| 5,827,323 A | 10/1998 | Klieman et al. |
| 5,836,868 A | 11/1998 | Ressemann et al. |
| 5,899,915 A | 5/1999 | Saadat |
| 5,913,867 A | 6/1999 | Dion |
| 6,015,420 A | 1/2000 | Wulfman et al. |
| 6,017,354 A | 1/2000 | Culp et al. |
| 6,086,608 A | 7/2000 | Ek et al. |
| 6,102,926 A | 8/2000 | Tartaglia et al. |
| 6,106,301 A | 8/2000 | Merril |
| 6,113,615 A | 9/2000 | Wulfman |
| 6,120,515 A | 9/2000 | Rogers et al. |
| 6,126,667 A | 10/2000 | Barry et al. |
| 6,139,510 A | 10/2000 | Palermo |
| 6,149,663 A | 11/2000 | Strandberg et al. |
| 6,171,312 B1 | 1/2001 | Beaty |
| 6,200,329 B1 | 3/2001 | Fung et al. |
| 6,234,725 B1 | 5/2001 | Campian |
| 6,270,509 B1 | 8/2001 | Barry et al. |
| 6,312,438 B1 | 11/2001 | Adams |
| 6,494,888 B1 | 12/2002 | Laufer et al. |
| 6,500,186 B2 | 12/2002 | Lafontaine et al. |
| 6,503,227 B1 | 1/2003 | Guo et al. |
| 6,503,261 B1 | 1/2003 | Bruneau et al. |
| 6,506,196 B1 | 1/2003 | Laufer |
| 6,554,845 B1 | 4/2003 | Fleenor et al. |
| 6,569,085 B2 | 5/2003 | Kortenbach et al. |
| 6,579,298 B1 | 6/2003 | Peskin et al. |
| 6,626,917 B1 | 9/2003 | Craig |
| 6,632,230 B2 | 10/2003 | Barry |
| 6,663,639 B1 | 12/2003 | Laufer et al. |
| 6,719,763 B2 | 4/2004 | Chung et al. |
| 6,740,030 B2 | 5/2004 | Martone et al. |
| 6,746,457 B2 | 6/2004 | Dana et al. |
| 6,755,843 B2 | 6/2004 | Chung et al. |
| 6,773,441 B1 | 8/2004 | Laufer et al. |
| 6,808,491 B2 | 10/2004 | Kortenbach et al. |
| 6,818,001 B2 | 11/2004 | Wulfman et al. |
| 6,821,285 B2 | 11/2004 | Laufer et al. |
| 6,835,200 B2 | 12/2004 | Laufer et al. |
| 6,908,427 B2 | 6/2005 | Fleener et al. |
| 6,997,931 B2 | 2/2006 | Sauer et al. |
| 7,056,284 B2 | 6/2006 | Martone et al. |
| 7,063,710 B2 | 6/2006 | Takamoto et al. |
| 7,063,715 B2 | 6/2006 | Onuki et al. |
| 7,094,246 B2 | 8/2006 | Anderson et al. |
| 7,144,401 B2 | 12/2006 | Yamamoto et al. |
| 7,147,646 B2 | 12/2006 | Dana et al. |
| 7,153,314 B2 | 12/2006 | Laufer et al. |
| 7,220,266 B2 | 5/2007 | Gambale |
| 7,232,445 B2 | 6/2007 | Kortenbach et al. |
| 7,235,086 B2 | 6/2007 | Sauer et al. |
| 7,285,130 B2 | 10/2007 | Austin |
| 7,326,221 B2 | 2/2008 | Sakamoto et al. |
| 7,344,545 B2 | 3/2008 | Takemoto et al. |
| 7,347,863 B2 | 3/2008 | Rothe et al. |
| 7,361,180 B2 | 4/2008 | Saadat et al. |
| 7,530,985 B2 | 5/2009 | Takemoto et al. |
| 7,601,161 B1 | 10/2009 | Nobles et al. |
| 7,618,425 B2 | 11/2009 | Yamamoto et al. |
| 7,713,277 B2 | 5/2010 | Laufer et al. |
| 7,722,633 B2 | 5/2010 | Laufer et al. |
| 7,727,246 B2 | 6/2010 | Sixto, Jr. et al. |
| 7,736,373 B2 | 6/2010 | Laufer et al. |
| 7,776,057 B2 | 8/2010 | Laufer et al. |
| 7,776,066 B2 | 8/2010 | Onuki et al. |
| 7,842,051 B2 | 11/2010 | Dana et al. |
| 7,846,180 B2 | 12/2010 | Cerier |
| 7,857,823 B2 | 12/2010 | Laufer et al. |
| 7,896,893 B2 | 3/2011 | Laufer et al. |
| 7,918,867 B2 | 4/2011 | Dana et al. |
| 7,951,157 B2 | 5/2011 | Gambale |
| 7,992,571 B2 | 8/2011 | Gross et al. |
| 7,993,368 B2 | 8/2011 | Gambale et al. |
| 8,016,840 B2 | 9/2011 | Takemoto et al. |
| 8,021,376 B2 | 9/2011 | Takemoto et al. |
| 8,057,494 B2 | 11/2011 | Laufer et al. |
| 8,062,314 B2 | 11/2011 | Sixto, Jr. et al. |
| 8,066,721 B2 | 11/2011 | Kortenbach et al. |
| 8,087,856 B2 | 1/2012 | Reed |
| 8,105,355 B2 | 1/2012 | Page et al. |
| 8,211,123 B2 | 7/2012 | Gross et al. |
| 8,216,253 B2 | 7/2012 | Saadat et al. |
| 8,226,667 B2 | 7/2012 | Viola et al. |
| 8,277,468 B2 | 10/2012 | Laufer et al. |
| 8,287,554 B2 | 10/2012 | Cerier et al. |
| 8,287,556 B2 | 10/2012 | Gilkey et al. |
| 8,308,765 B2 | 11/2012 | Saadat et al. |
| 8,313,496 B2 | 11/2012 | Sauer et al. |
| 8,361,089 B2 | 1/2013 | Chu |
| 8,388,632 B2 | 3/2013 | Gambale |
| 8,425,555 B2 | 4/2013 | Page et al. |
| 8,454,631 B2 | 6/2013 | Viola et al. |
| 8,480,691 B2 | 7/2013 | Dana et al. |
| 8,540,735 B2 | 9/2013 | Mitelberg et al. |
| 8,551,120 B2 | 10/2013 | Gambale |
| 8,556,914 B2 | 10/2013 | Vrba |
| 8,585,720 B2 | 11/2013 | Gross et al. |
| 8,603,123 B2 | 12/2013 | Todd |
| 8,632,553 B2 | 1/2014 | Sakamoto et al. |
| 8,679,136 B2 | 3/2014 | Mitelberg |
| 8,709,022 B2 | 4/2014 | Stone et al. |
| 8,764,771 B2 | 7/2014 | Chu |
| 8,882,785 B2 | 11/2014 | Dicesare et al. |
| 8,926,634 B2 | 1/2015 | Rothe et al. |
| 8,992,570 B2 | 3/2015 | Gambale et al. |
| 9,011,466 B2 | 4/2015 | Overes et al. |
| 9,050,126 B2 | 6/2015 | Rivers et al. |
| 9,050,127 B2 | 6/2015 | Bonnette et al. |
| 9,089,325 B2 | 7/2015 | Mitelberg et al. |
| 9,125,646 B2 | 9/2015 | Woodard, Jr. et al. |
| 9,198,562 B2 | 12/2015 | Mitelberg et al. |
| 9,232,957 B2 | 1/2016 | Adams |
| 9,320,515 B2 | 4/2016 | Dana et al. |
| 9,474,536 B2 | 10/2016 | Carrison et al. |
| 9,486,126 B2 | 11/2016 | West et al. |
| 9,504,465 B2 | 11/2016 | Chu |
| 9,510,817 B2 | 12/2016 | Saadat et al. |
| 9,526,519 B2 | 12/2016 | Kessler et al. |
| 9,549,728 B2 | 1/2017 | Chu |
| 9,750,494 B2 | 9/2017 | Gross et al. |

(56) References Cited

U.S. PATENT DOCUMENTS

| | | | |
|---|---|---|---|
| 9,788,831 B2 | 10/2017 | Mitelberg | |
| 9,844,366 B2 | 12/2017 | Woodard, Jr. et al. | |
| 9,867,610 B2 | 1/2018 | Mitelberg et al. | |
| 9,931,488 B2 | 4/2018 | Bunch et al. | |
| 10,045,871 B2 | 8/2018 | Saadat et al. | |
| 10,052,122 B2 | 8/2018 | Higgins et al. | |
| 10,130,437 B2 | 11/2018 | Lee et al. | |
| 10,143,463 B2 | 12/2018 | Dana et al. | |
| 10,194,902 B2 | 2/2019 | Nobles et al. | |
| 10,335,142 B2 | 7/2019 | Raybin et al. | |
| 10,503,199 B1* | 12/2019 | Cone | G05G 1/305 |
| 10,722,250 B2 | 7/2020 | Tasci et al. | |
| 10,736,628 B2 | 8/2020 | Yates et al. | |
| 2001/0004700 A1 | 6/2001 | Honeycutt et al. | |
| 2001/0037121 A1 | 11/2001 | McGuckin, Jr. et al. | |
| 2002/0007190 A1 | 1/2002 | Wulfman et al. | |
| 2002/0058956 A1 | 5/2002 | Honeycutt et al. | |
| 2002/0107530 A1 | 8/2002 | Sauer et al. | |
| 2002/0151917 A1* | 10/2002 | Barry | A61B 17/320758 |
| | | | 606/159 |
| 2002/0161384 A1 | 10/2002 | Wulfman et al. | |
| 2003/0093103 A1 | 5/2003 | Malackowski et al. | |
| 2003/0204205 A1 | 10/2003 | Sauer et al. | |
| 2004/0002699 A1 | 1/2004 | Ryan et al. | |
| 2004/0068270 A1 | 4/2004 | Alfred, III | |
| 2004/0138706 A1 | 7/2004 | Abrams et al. | |
| 2004/0186368 A1 | 9/2004 | Ramzipoor et al. | |
| 2005/0004579 A1 | 1/2005 | Schneider et al. | |
| 2005/0015021 A1 | 1/2005 | Shiber | |
| 2005/0033319 A1 | 2/2005 | Gambale et al. | |
| 2005/0240146 A1 | 10/2005 | Nash et al. | |
| 2005/0250985 A1 | 11/2005 | Saadat et al. | |
| 2006/0074405 A1 | 4/2006 | Malackowski et al. | |
| 2006/0074442 A1 | 4/2006 | Noriega et al. | |
| 2006/0142775 A1 | 6/2006 | Heneberry et al. | |
| 2006/0282094 A1 | 12/2006 | Stokes et al. | |
| 2007/0093841 A1 | 4/2007 | Hoogland | |
| 2007/0239140 A1* | 10/2007 | Chechelski | A61B 17/320758 |
| | | | 606/1 |
| 2007/0270908 A1 | 11/2007 | Stokes et al. | |
| 2008/0039823 A1 | 2/2008 | Shimogami et al. | |
| 2008/0086148 A1 | 4/2008 | Baker et al. | |
| 2008/0097499 A1 | 4/2008 | Nash et al. | |
| 2008/0146965 A1 | 6/2008 | Privitera et al. | |
| 2009/0024085 A1 | 1/2009 | To et al. | |
| 2009/0069829 A1 | 3/2009 | Shturman | |
| 2009/0124975 A1 | 5/2009 | Oliver et al. | |
| 2009/0177031 A1 | 7/2009 | Surti et al. | |
| 2010/0125276 A1 | 5/2010 | Palermo | |
| 2010/0137681 A1 | 6/2010 | Ewers et al. | |
| 2010/0198006 A1 | 8/2010 | Greenburg et al. | |
| 2010/0312263 A1 | 12/2010 | Moberg et al. | |
| 2011/0077673 A1 | 3/2011 | Grubac et al. | |
| 2011/0213391 A1 | 9/2011 | Rivers et al. | |
| 2011/0251554 A1* | 10/2011 | Romoscanu | A61M 25/0136 |
| | | | 604/95.04 |
| 2011/0306995 A1 | 12/2011 | Moberg | |
| 2012/0053606 A1 | 3/2012 | Schmitz et al. | |
| 2012/0095461 A1 | 4/2012 | Herscher et al. | |
| 2012/0130410 A1 | 5/2012 | Tal et al. | |
| 2012/0136348 A1 | 5/2012 | Condie et al. | |
| 2012/0158023 A1 | 6/2012 | Mitelberg et al. | |
| 2012/0172963 A1 | 7/2012 | Ryan et al. | |
| 2012/0179167 A1 | 7/2012 | Wenderow et al. | |
| 2012/0185031 A1 | 7/2012 | Ryan et al. | |
| 2012/0209176 A1 | 8/2012 | Anderson | |
| 2012/0271327 A1 | 10/2012 | West et al. | |
| 2013/0006248 A1 | 1/2013 | Ellis | |
| 2013/0079763 A1 | 3/2013 | Heckel et al. | |
| 2013/0096581 A1 | 4/2013 | Gilkey et al. | |
| 2013/0103062 A1 | 4/2013 | To et al. | |
| 2013/0253552 A1 | 9/2013 | Schoenle et al. | |
| 2013/0274657 A1 | 10/2013 | Zirps et al. | |
| 2013/0304093 A1 | 11/2013 | Serina et al. | |
| 2014/0100574 A1 | 4/2014 | Bono et al. | |

| | | | |
|---|---|---|---|
| 2014/0128668 A1 | 5/2014 | Cox et al. | |
| 2014/0148835 A1 | 5/2014 | Schmitz et al. | |
| 2014/0212457 A1 | 7/2014 | Rifai | |
| 2014/0222042 A1 | 8/2014 | Kessler et al. | |
| 2014/0249554 A1 | 9/2014 | To et al. | |
| 2014/0261453 A1 | 9/2014 | Carlson | |
| 2014/0276933 A1* | 9/2014 | Hart | A61M 25/0147 |
| | | | 606/130 |
| 2014/0277014 A1 | 9/2014 | Higgins et al. | |
| 2014/0316447 A1 | 10/2014 | Ellering et al. | |
| 2014/0316448 A1 | 10/2014 | Higgins | |
| 2014/0316451 A1 | 10/2014 | Higgins et al. | |
| 2014/0324052 A1 | 10/2014 | Carrison et al. | |
| 2015/0011834 A1 | 1/2015 | Ayala et al. | |
| 2015/0073448 A1 | 3/2015 | Rydberg | |
| 2015/0125807 A1 | 5/2015 | Shipley | |
| 2015/0126983 A1 | 5/2015 | Alvarado et al. | |
| 2015/0164540 A1 | 6/2015 | Higgins et al. | |
| 2015/0173776 A1 | 6/2015 | Burke et al. | |
| 2015/0173838 A1 | 6/2015 | Murphy et al. | |
| 2015/0201956 A1 | 7/2015 | Higgins et al. | |
| 2015/0216554 A1 | 8/2015 | Kessler et al. | |
| 2015/0289946 A1* | 10/2015 | Johansson | A61B 34/25 |
| | | | 434/262 |
| 2015/0327880 A1 | 11/2015 | Wasicek et al. | |
| 2015/0335348 A1 | 11/2015 | Cohen et al. | |
| 2016/0022307 A1 | 1/2016 | Wasdyke et al. | |
| 2016/0045197 A1 | 2/2016 | Mitelberg et al. | |
| 2016/0157886 A1 | 6/2016 | WasDyke et al. | |
| 2016/0235434 A1 | 8/2016 | Smith et al. | |
| 2016/0235441 A1 | 8/2016 | Parkin | |
| 2016/0287284 A1 | 10/2016 | Smith et al. | |
| 2016/0346003 A1 | 12/2016 | Grothe et al. | |
| 2016/0354107 A1 | 12/2016 | Nakano et al. | |
| 2016/0354108 A1* | 12/2016 | Nakano | A61B 17/320758 |
| 2017/0086817 A1 | 3/2017 | Mitelberg | |
| 2017/0086818 A1 | 3/2017 | Mitelberg | |
| 2017/0181760 A1 | 6/2017 | Look et al. | |
| 2017/0189123 A1 | 7/2017 | Govari et al. | |
| 2017/0273698 A1 | 9/2017 | McGuckin, Jr. et al. | |
| 2017/0296200 A1 | 10/2017 | Singer et al. | |
| 2018/0042602 A1 | 2/2018 | Mitelberg et al. | |
| 2018/0042603 A1 | 2/2018 | Mitelberg et al. | |
| 2018/0153381 A1 | 6/2018 | Wei et al. | |
| 2018/0183179 A1 | 6/2018 | Byrd et al. | |
| 2018/0193056 A1 | 7/2018 | Colyer et al. | |
| 2018/0235604 A1 | 8/2018 | Comee et al. | |
| 2018/0242998 A1 | 8/2018 | Dhandhusaria et al. | |
| 2019/0142526 A1 | 5/2019 | Hendrick et al. | |
| 2019/0175211 A1 | 6/2019 | Carlson et al. | |
| 2019/0262032 A1 | 8/2019 | Carlson et al. | |
| 2019/0262034 A1* | 8/2019 | Spangler | A61B 34/76 |
| 2020/0022764 A1 | 1/2020 | Flexman et al. | |
| 2020/0060718 A1 | 2/2020 | Patel et al. | |
| 2020/0069324 A1 | 3/2020 | Deepa | |
| 2020/0229844 A1 | 7/2020 | Rawson et al. | |
| 2020/0315654 A1 | 10/2020 | Patel et al. | |
| 2020/0367984 A1* | 11/2020 | Peine | B25J 9/1666 |
| 2021/0077143 A1 | 3/2021 | Neuharth et al. | |
| 2021/0172499 A1 | 6/2021 | Nino | |
| 2022/0218385 A1 | 7/2022 | Hilse et al. | |

FOREIGN PATENT DOCUMENTS

| | | | |
|---|---|---|---|
| EP | 1520509 A1 | 4/2005 | |
| EP | 2011446 A2 | 7/2009 | |
| EP | 2108304 A2 | 10/2009 | |
| EP | 2508141 A1 | 10/2012 | |
| EP | 3053534 A1 | 8/2016 | |
| EP | 3132760 A1 | 2/2017 | |
| EP | 3192461 A1 | 7/2017 | |
| EP | 3222228 A1 | 9/2017 | |
| EP | 3226784 B1 | 9/2020 | |
| IE | S2009529 A2 | 4/2012 | |
| JP | H10174689 A | 6/1998 | |
| JP | 2001509685 A | 7/2001 | |
| WO | 9629014 A1 | 9/1996 | |
| WO | 9814124 A1 | 4/1998 | |
| WO | 0051511 A1 | 9/2000 | |

(56)                    References Cited

FOREIGN PATENT DOCUMENTS

| WO | 0056230 | A2 | 9/2000 |
|----|---------|----|--------|
| WO | 2001054595 | A1 | 8/2001 |
| WO | 0189393 | A1 | 11/2001 |
| WO | 0249518 | A2 | 6/2002 |
| WO | 2004080507 | A2 | 9/2004 |
| WO | 2008016592 | A2 | 2/2008 |
| WO | 2008045376 | A2 | 4/2008 |
| WO | 2008098124 | A1 | 8/2008 |
| WO | 2010036227 | A1 | 4/2010 |
| WO | 2010056714 | A1 | 5/2010 |
| WO | 2010089727 | A1 | 8/2010 |
| WO | 2011060192 | A1 | 5/2011 |
| WO | 2011106053 | A1 | 9/2011 |
| WO | 2013158849 | A2 | 10/2013 |
| WO | 2014106847 | A1 | 7/2014 |
| WO | 2016001932 | A1 | 1/2016 |
| WO | 2016144834 | A1 | 9/2016 |
| WO | 2016200811 | A1 | 12/2016 |
| WO | 2017087856 | A1 | 5/2017 |
| WO | 2018156603 | A1 | 8/2018 |
| WO | 2019118522 | A1 | 6/2019 |
| WO | 2019168784 | A1 | 9/2019 |
| WO | 2020055728 | A1 | 3/2020 |
| WO | 2020223433 | A1 | 11/2020 |

OTHER PUBLICATIONS

International Search Report and Written Opinion dated Oct. 1, 2019 for International Application No. PCT/US2019/038006.

Invitation to Pay Additional Fees dated Sep. 26, 2019 for International Application No. PCT/US2019/037995.

International Search Report and Written Opinion dated Dec. 6, 2019 for International Application No. PCT/US2019/037995.

Invitation to Pay Additional Fees dated Nov. 18, 2019 for International Application No. PCT/US2019/049774.

International Search and Written Opinion dated Sep. 20, 2019 for International Application No. PCT/2019/039312.

International Search Report and Written Opinion dated Jun. 4, 2021 for International Application No. PCT/US2021/017939.

International Search Report and Written opinion dated Mar. 28, 2018 for International Application No. PCT/US2018/013587.

International Search Report and Written Opinion dated Apr. 17, 2019 for International Application No. PCT/US2019/018121.

International Search Report and Written Opinion dated Apr. 26, 2019, for International Application No. PCT/US2019/019404.

"What is a PID Controller: Working & Its Applications, 2013, EL-PRO-CUS, URL:https://www.elprocus.com/the-working-of-a-pid-controller/" 17 pages, (Year:2013).

International Search Report and Written Opinion dated Apr. 26, 2019, for International Application No. PCT/US2019/019631.

International Search Report and Written Opinion dated Apr. 26, 2019, for International Application No. PCT/US2019/0198848.

International Search Report and Written Opinion dated Mar. 30, 2020 for International Application No. PCT/US2020/014062.

International Search Report and Written Opinion dated Jun. 25, 2020 for International Application No. PCT/US2020/012767.

International Search Report and Written Opinion dated Apr. 22, 2020 for International Application No. PCT/US2020/013764.

International Search Report and Written Opinion dated Jun. 24, 2020 for International Application No. PCT/US2020/027079.

International Search Report and Written Opinion dated Sep. 4, 2020 for International Application No. PCT/US2020/038132.

International Search Report and Written Opinion dated Sep. 7, 2020 for International Application No. PCT/US2020/038145.

International Search Report and Written Opinion dated Dec. 8, 2020 for International Application No. PCT/US2020/049999.

Invite to Pay Additional Fees dated Feb. 16, 2021 for International Application No. PCT/US2020/061383.

International Search Report and Written Opinion dated Feb. 22, 2022 for International Application No. PCT/US2021/057279.

International Search Report and Written Opinion dated Jan. 26, 2022 for International Application No. PCT/US2021/056616.

International Search Report and Written Opinion dated Oct. 17, 2022 for International Application No. PCT/US2022/041260.

International Search Report and Written Opinion dated Nov. 8, 2022 for International Application No. PCT/US2022/041263.

* cited by examiner

FLY BY WIRE CONTROL FOR ATHERECTOMY

CROSS-REFERENCE TO RELATED APPLICATIONS

This application claims the benefit of priority under 35 U.S.C. § 119 of U.S. Provisional Application No. 63/257,681, filed Oct. 20, 2021, the entire disclosure of which is hereby incorporated by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

SUMMARY

This disclosure provides design, material, manufacturing method, and use alternatives for medical devices. As an example, an atherectomy system includes an advancer assembly and a drive assembly that is adapted to translates relative to the advancer assembly. The drive assembly includes a drive shaft operably coupled with the drive assembly such that the drive shaft translates with the drive assembly. An operator assembly includes a user interface that an operator engages with in order to indicate requested movement of the drive assembly, the user interface configured to output a request signal indicating requested movement of the drive assembly. One or more sensors are adapted to ascertain one or more conditions of the drive assembly and to output one or more condition signals. A controller is operably coupled with the operator assembly and the drive assembly. The controller is adapted to receive the request signal from the operator assembly and the one or more condition signals, to determine a command signal in response to the received request signal and the received one or more condition signals, and to provide the command signal to the drive assembly. The drive assembly is adapted to move relative to the advancer assembly in accordance with the command signal.

Alternatively or additionally, the atherectomy system may further include a servo motor that is adapted to move the drive assembly relative to the advancer assembly in response to the command signal.

Alternatively or additionally, one of the one or more sensors may include a servo force sensor that is adapted to provide the controller with a force signal indicating resistance to movement of the drive assembly relative to the advancer assembly.

Alternatively or additionally, the drive assembly may further include a drive motor adapted to rotate the drive shaft.

Alternatively or additionally, one of the one or more sensors may include a drive motor sensor that is adapted to provide the controller with a drive motor condition signal indicating a current operating condition of the drive motor.

Alternatively or additionally, one of the one or more sensors may include a drive assembly position sensor that is adapted to provide the controller with a drive assembly position signal indicating a relative position of the drive assembly.

Alternatively or additionally, the atherectomy system may further include a feedback generator that is adapted to change a feel of the user interface in order to indicate a sensed condition of the drive assembly.

Alternatively or additionally, the feedback generator may include an active feedback generator.

Alternatively or additionally, the controller may be further adapted to determine an active feedback generation signal based upon signals received from the one or more sensors adapted to ascertain one or more conditions of the drive assembly and to provide the active feedback generation signal to the active feedback generator, where the active feedback generator is adapted to generate feedback to the user interface in accordance with the active feedback generation signal.

Alternatively or additionally, the controller may be further adapted to determine the active feedback generation signal in accordance with a first set of tuning parameter values when the operator is requesting that the drive assembly move in an anterograde ablation direction, and to determine the active feedback generation signal in accordance with a second set of tuning parameter values, different from the first set of tuning parameter values, when the operator is requesting that the drive assembly move in a retrograde ablation direction.

Alternatively or additionally, the controller may be further adapted to provide relatively less feedback to the user interface via the active feedback generator when the operator is requesting relatively low force movement of the drive assembly and to provide relatively greater feedback to the user interface via the active feedback generator when the operator is requesting relatively high force movement of the drive assembly.

Alternatively or additionally, the controller may be further adapted to provide relatively less feedback to the user interface via the active feedback generator when the operator is requesting that the drive assembly move in the anterograde ablation direction and to provide relatively more feedback to the user interface via the active feedback generator when the operator is requesting that the drive assembly move in the retrograde ablation direction.

Alternatively or additionally, the atherectomy system may further include an atherectomy burr that is adapted to be secured to the drive shaft and that includes a tapered body including a proximal taper and a distal taper, a first ablating surface disposed on the proximal taper for retrograde ablation, and a second ablating surface disposed on the distal taper for anterograde ablation.

Alternatively or additionally, the controller may be further adapted to engage a fail-safe operation in the event that communication between the controller and any of the one or more sensors is lost.

Alternatively or additionally, the operator assembly may further include a user interface position sensor that provides the controller with a signal indicating a current position of the user interface.

As another example, an atherectomy system is adapted for both anterograde direction ablation and for retrograde direction ablation. The atherectomy system includes an operator assembly and an advancer assembly. The operator assembly includes a user interface that an operator engages with in order to indicate requested movement of the drive assembly, the user interface configured to output a request signal indicating requested movement of the drive assembly. The operator assembly also includes a first controller operably coupled with the operator assembly and adapted to receive the request signal from the user interface. The advancer assembly includes a drive assembly adapted to translate relative to the advancer assembly, the drive assembly including a drive shaft operably coupled with the drive assembly such that the drive shaft translates with the drive assembly. The advancer assembly includes one or more sensors adapted to ascertain one or more conditions of the drive assembly and to output one or more condition signals. The advancer assembly also includes a second controller operably coupled with the operator assembly and the drive assembly. The second controller is adapted to receive the request signal from the first controller and the one or more condition signals, determine a command signal in response to the received request signal and the received one or more condition signals, and provide the command signal to the drive assembly. The drive assembly is adapted to move relative to the advancer assembly in accordance with the command signal.

Alternatively or additionally, the first controller and the second controller may each be adapted to communicate wirelessly with each other.

Alternatively or additionally, the operator assembly may further include an active feedback generator operably coupled with the user interface.

Alternatively or additionally, the atherectomy system further includes an atherectomy burr that is adapted to be secured to the drive shaft and that includes a tapered body including a proximal taper and a distal taper, a first ablating surface disposed on the proximal taper for retrograde ablation and a second ablating surface disposed on the distal taper for anterograde ablation.

As another example, an atherectomy system includes an advancer assembly and a drive assembly that is adapted to translate relative to the advancer assembly, the drive assembly including a drive shaft operably coupled with the drive assembly such that the drive shaft translates with the drive assembly. The atherectomy system includes an operator assembly including a user interface that an operator engages with in order to indicate requested movement of the drive assembly, the user interface configured to output a request signal indicating requested movement of the drive assembly, and an active feedback generator operably coupled with the user interface, the active feedback generator adapted to alter a feel of the user interface in response to a received feedback signal. One or more sensors are adapted to ascertain one or more conditions of the drive assembly and to output one or more condition signals. A controller is operably coupled with the operator assembly and the drive assembly and is adapted to receive the request signal from the operator assembly and the one or more condition signals, determine a command signal in response to the received request signal and the received one or more condition signals, determine the feedback signal, provide the command signal to the drive assembly, and provide the feedback signal to the active feedback generator, where the drive assembly is adapted to move relative to the advancer assembly in accordance with the command signal.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
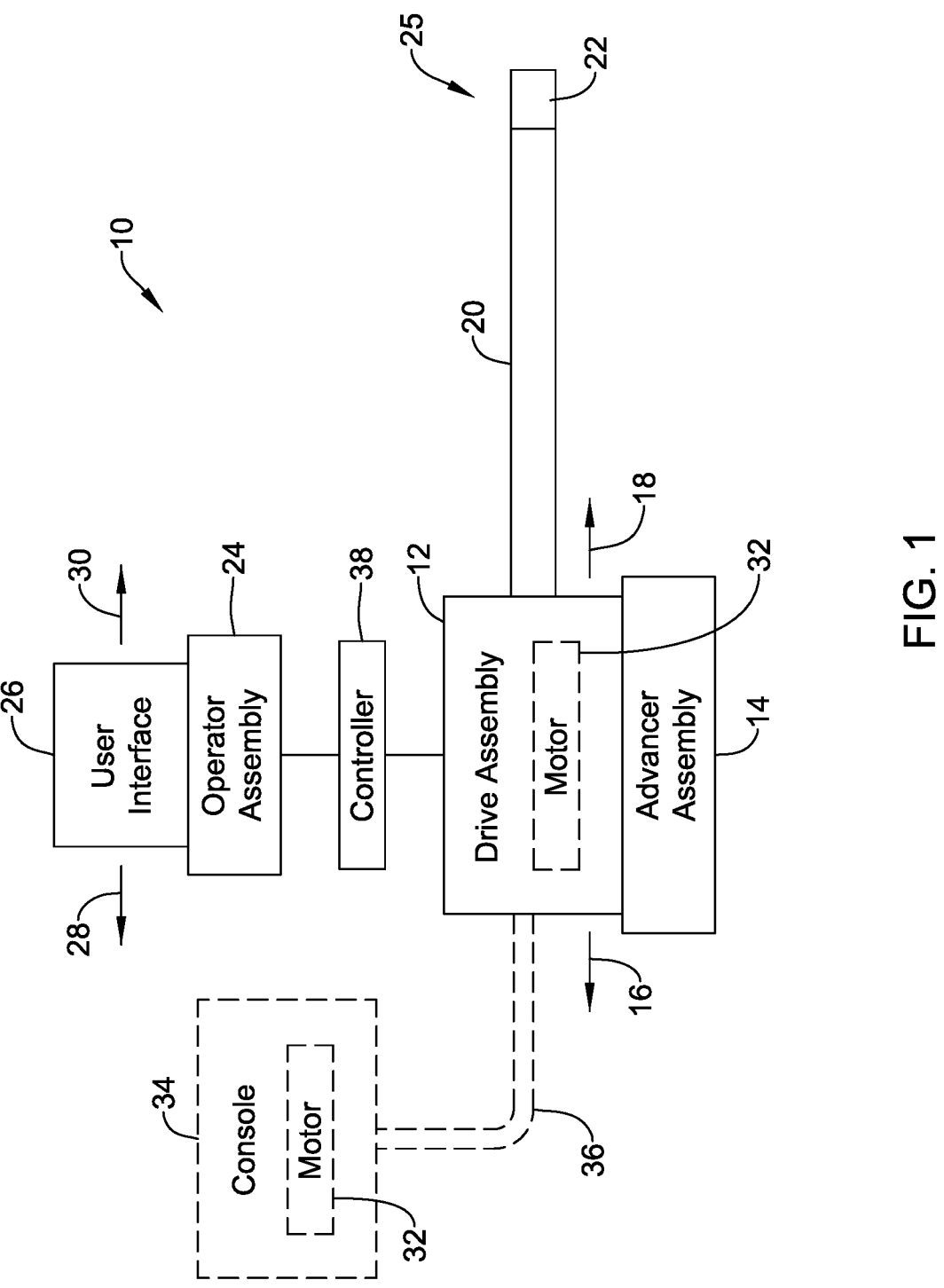
FIG. 1 is a schematic block diagram of an illustrative atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits may restrict blood flow and can cause ischemia in a heart of a patient, vasculature of a patient's legs, a patient's carotid artery, etc. Such ischemia may lead to pain, swelling, wounds that will not heal, amputation, stroke, myocardial infarction, and/or other conditions.

Atheromatous deposits may have widely varying properties, with some deposits being relatively soft and others being fibrous and/or calcified. In the latter case, the deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and/or a variety of catheter-based approaches that may rely on intravascular widening or removal of the atheromatous or other material occluding the blood vessel. Atherectomy is a catheter-based intervention that may be used to treat atherosclerosis.

Atherectomy is an interventional medical procedure performed to restore a flow of blood through a portion of a patient's vasculature that has been blocked by plaque or other material (e.g., blocked by an occlusion). In an atherectomy procedure, a device on an end of a drive shaft that is used to engage and/or remove (e.g., abrade, grind, cut, shave, etc.) plaque or other material from a patient's vessel (e.g., artery or vein). In some cases, the device on an end of the drive shaft may be abrasive and/or may otherwise be a configured to remove plaque from a vessel wall or other obstruction in a vessel when the device is rotating and engages the plaque or other obstruction. In some cases, atherectomy involves using an abrasive atherectomy burr that is rotated at high speeds exceeding 100,000 revolutions per minute (RPM) in order to abrade plaque and other hardened materials from within the patient's vessel. Atherectomy burrs may be rotated at speeds exceeding 140,000 RPM, at speeds exceeding 180,000 RPM and even at speeds as high as 220,000 RPM. Atherectomy may include orbital atherectomy in addition to rotational atherectomy.

FIG. 1 is a schematic block diagram of an illustrative atherectomy system 10. The illustrative atherectomy system 10 includes a drive assembly 12 that is adapted to be translatingly secured relative to an advancer assembly 14. In some cases, the advancer assembly 14 may be adapted to be fixed in space, such as being secured to a table, for example. In some cases, the advancer assembly 14 may be part of an advancer handle. The drive assembly 12 may also be disposed within an advancer handle, for example, but is adapted to translate back and forth (left and right in the illustrated orientation) as indicated by arrows 16 and 18, respectively. A drive shaft 20 extends distally from the drive assembly 12. An atherectomy burr 22 is secured to a distal end 25 of the drive shaft 20. While not illustrated, the drive shaft 20 includes a lumen that allows the drive shaft 20 to be advanced over a guidewire to reach a treatment site as well as to rotate with respect to the guidewire.

It will be appreciated that the drive shaft 20, which is shown schematically, may include additional components. For example, the drive shaft 20 may include an outer sheath (not shown). In some cases, the outer sheath may be adapted to allow the drive shaft 20 to rotate within the outer sheath. The outer sheath may be secured relative to the drive assembly 12 such that the outer sheath moves left and right as the drive assembly 12 (and hence the drive shaft 20)

moves left and right. As a result, the position of the atherectomy burr 22 relative to the outer sheath does not change. In some cases, the outer sheath may instead be secured relative to the advancer assembly 14 such that the drive shaft 20 is able to rotate within the outer sheath. The outer sheath may remain stationary while the drive assembly 12 translates left and right. This means that the position of the atherectomy burr 22 relative to the outer sheath does change.

The atherectomy system 10 includes an operator assembly 24 that has a user interface 26. The operator assembly 24 may be adapted to be hand-held. In some instances, the operator assembly 24 may be adapted to be secured to a work surface. In some instances, the user interface 26 may be considered as taking the form of a joystick or other game controller. In some cases, the user interface 26 may be a knob that is easily grasped by an operator operating the atherectomy system 10. The user interface 26 may include a knob that slides back and forth, or perhaps a knob that rotates. The user interface 26 may include a lever that can be moved to indicate a forward direction or a backward direction. In some cases, the user interface 26 may include a touch sensitive controller or even a touch screen. Moving the user interface 26 back and forth in the directions indicated by arrows 28 and 30 may cause the operator assembly 24 to output a request signal for the drive assembly 12 to correspondingly move the drive assembly 12 back and forth in the directions indicated by the arrows 16 and 18, respectively, as will be discussed.

The drive assembly 12 may include a drive motor 32, such as an electric drive motor, a pneumatic drive motor, a hydraulic drive motor or even a windup drive motor. The drive motor 32 may be disposed within the drive assembly 12, as shown in phantom. In some cases, the drive motor 32 may not be disposed within the drive assembly 12, but may instead be remotely located within a console 34, with a flexible drive cable 36 extending from the drive motor 32 to the drive assembly 12.

In some cases, the drive motor and other components, such as but not limited to a controller that is adapted to regulate operation of the drive motor, may be disposed in a reusable assembly that either remains outside of the sterile field during use, or may be bagged or otherwise sealed for use within the sterile field. In some cases, a reusable assembly may be adapted to be sterilized a plurality of times and thus can be used for more than one patient. In some cases, at least some of the drive assembly 12, the advancer assembly 14, the drive shaft 20 and the atherectomy burr 22 may be considered as being part of a single use assembly, that is sterilizable for use with a single patient and then is disposed of. In some cases, the entire atherectomy system 10 may be considered to be adapted for single use. In some cases, the entire atherectomy system 10 may be considered to be adapted for multiple uses.

In some cases, the drive shaft 20 is a coil spring. It will be appreciated that a coil spring may have a first set of properties when under compression, such as when the drive shaft 20 is being advanced distally and the atherectomy burr 22 has reached an obstacle, and may have a second set of properties that are different from the first set of properties when under tension, such as when the drive shaft 20 is being withdrawn proximally and the atherectomy burr 22 has reached an obstacle. In some cases, while the drive shaft 20 is intended to rotate in a particular rotational direction when being used to drive the atherectomy burr 22, instances of excessive torque may cause the atherectomy system 10 to behave differently. For example, a controller regulating operation of the drive assembly 12 may stop the drive shaft 20 and may briefly reverse its rotational direction. It will be appreciated that this may cause the drive shaft 20 to alternate between winding, when driven in its primary direction, and unwinding, when either driven in a rotational direction opposite its primary direction or allowed to unwind on its own. It will be appreciated that the feel of the atherectomy system 10, as manifested in the force the user feels when trying to move the knob 26, may not be consistent depending on what the drive shaft 20 is doing.

In some cases, the atherectomy system 10 may provide a particular feedback to the user when the user is using the atherectomy system 10 to ablate in an anterograde direction, meaning advancing the atherectomy burr 22 in a distal direction into a lesion to be removed or reduced. In some cases, the feedback provided to the user during ablation in an anterograde direction provides predictability, i.e., the user learns to recognize how the feedback the user is receiving via the force the user is applying to the user interface 26 translates into what the drive shaft 20 is doing. The user learns that a particular application of force via the user interface 26 means that moving the atherectomy burr 22 a particular distance, for example. The feedback when ablating in the anterograde direction may be considered as largely being "linear".

However, in some cases there may be a desire to also be able to ablate in a retrograde direction, i.e., while moving the atherectomy burr 22 in a proximal direction. This may come about if the user applies too much force, and the atherectomy burr 22 pops through the lesion and ends up distal of the lesion. This is referred to as "watermelon seeding" the atherectomy burr 22. Alternatively or additionally, once a lesion is removed or reduced while ablating in an antero-grade direction, the atherectomy burr 22 may be translated distal to the lesion, such that on translation in the proximal direction, the atherectomy burr 22 is able to ablate in the retrograde direction. This is known as "polishing" the lesion. Ablation in both the anterograde direction and the retrograde direction can be advantageous relative to polishing solely in the anterograde direction. Ablating in a retrograde direction may provide the user with feedback that is less predictable and less "linear". Accordingly, there is a risk of providing too much force, which can cause potential tissue damage or even cause the atherectomy burr 22 to become stuck and in some instances occlude blood flow.

The atherectomy system 10 includes a controller 38 that receives the request signal from the operator assembly 24 and determines a corresponding command signal that will be sent to the drive assembly 12. The command signal may be based at least in part upon the request signal. The command signal may be based at least in part upon whether the operator is instructing, by movement of the user interface 26, to move the drive assembly 12 in an anterograde ablation direction or in a retrograde ablation direction. The command signal may be based at least in part upon signals received from one or more sensors (not shown) that provide the controller 38 with additional information regarding the performance of the atherectomy system 10. This may include, for example, the relative position of the drive assembly 12 relative to the advancer assembly 14. This may include, for example, information pertaining to how much force is being applied by the drive assembly 12, the rotational speed of the drive shaft 20, and the like.

In some cases, the controller 38 may be considered as being the connection between the operator assembly 24 and the advancer assembly 14, with the controller 38 operably disposed between the operator assembly 24 and the advancer assembly 14. The controller 38 may be part of the operator assembly 24. In some cases, the controller 38 may be part of the advancer assembly 14. In some cases, the controller 38 or at least the functionality thereof may reside in a remote computer, for example. In some cases, the controller 38 may not be a single controller, but may instead include a first controller that is operably coupled with the operator assembly 24 and a second controller that is operably coupled with the drive assembly 14.

In some instances, the operator assembly 24 may be close enough to the advancer assembly 14 to enable a physical connection via a cable extending therebetween. In some instances, the operator assembly 24 may be remote from the advancer assembly 14, and communication therebetween may be over a network such as a local area network (LAN) or a wide area network (WAN). In some cases, the Internet may be used to provide communication between the operator assembly 24 and the advancer assembly 14.

It will be appreciated that when the operator engages the user interface 26, they are not directly moving the drive assembly 12. Rather, moving or otherwise engaging the user interface 26 causes the request signal to be sent to the controller 38. The controller 38 uses the request signal, and perhaps additional inputs as well, to determine the corresponding command signal. The command signal is sent from the controller 38 to the drive assembly 12 and the drive assembly 12 responds appropriately. The atherectomy system 10 may be considered as functioning as a fly by wire atherectomy system in which there is no direct mechanical relationship between movement of the user interface 26 and corresponding movement of the drive assembly 12.

As a result of the controller 38 determining an appropriate command signal in response to receiving the request signal, it will be appreciated that the controller 38 is able to modify how the drive assembly 12 responds to a particular input. When the drive assembly 12 is moving in the anterograde ablation direction, the controller 38 may utilize a first set of tuning parameter values when determining the appropriate command signal and the controller 38 may utilize a second set of tuning parameter values when determining the appropriate command signal when ablating in the retrograde direction.

In some cases, as will be discussed, feedback may be provided to the user interface 26 in order to modify how the operator engages the user interface 26. For example, if the controller 38 determines that the operator is attempting to move the drive assembly too quickly, or too far, the controller 38 may generate an appropriate command that causes feedback to be provided to the user interface 26. If the operator is pushing too hard, for example, the feedback may increase the relative force, or resistance to movement, that the operator may feel via the user interface 26. How the feedback is created will be discussed subsequently.

In some cases, feedback may be passive. In some instances, feedback may be active, meaning that the feedback changes in accordance with current operating conditions. Some details regarding feedback may be found in U.S. 62/237,679 filed Aug. 27, 2021 and entitled ATHEREC-TOMY SYSTEM WITH ANTEROGRADE AND RETRO-GRADE ABLATION, which application is incorporated by reference herein in its entirety.

Figure 2:
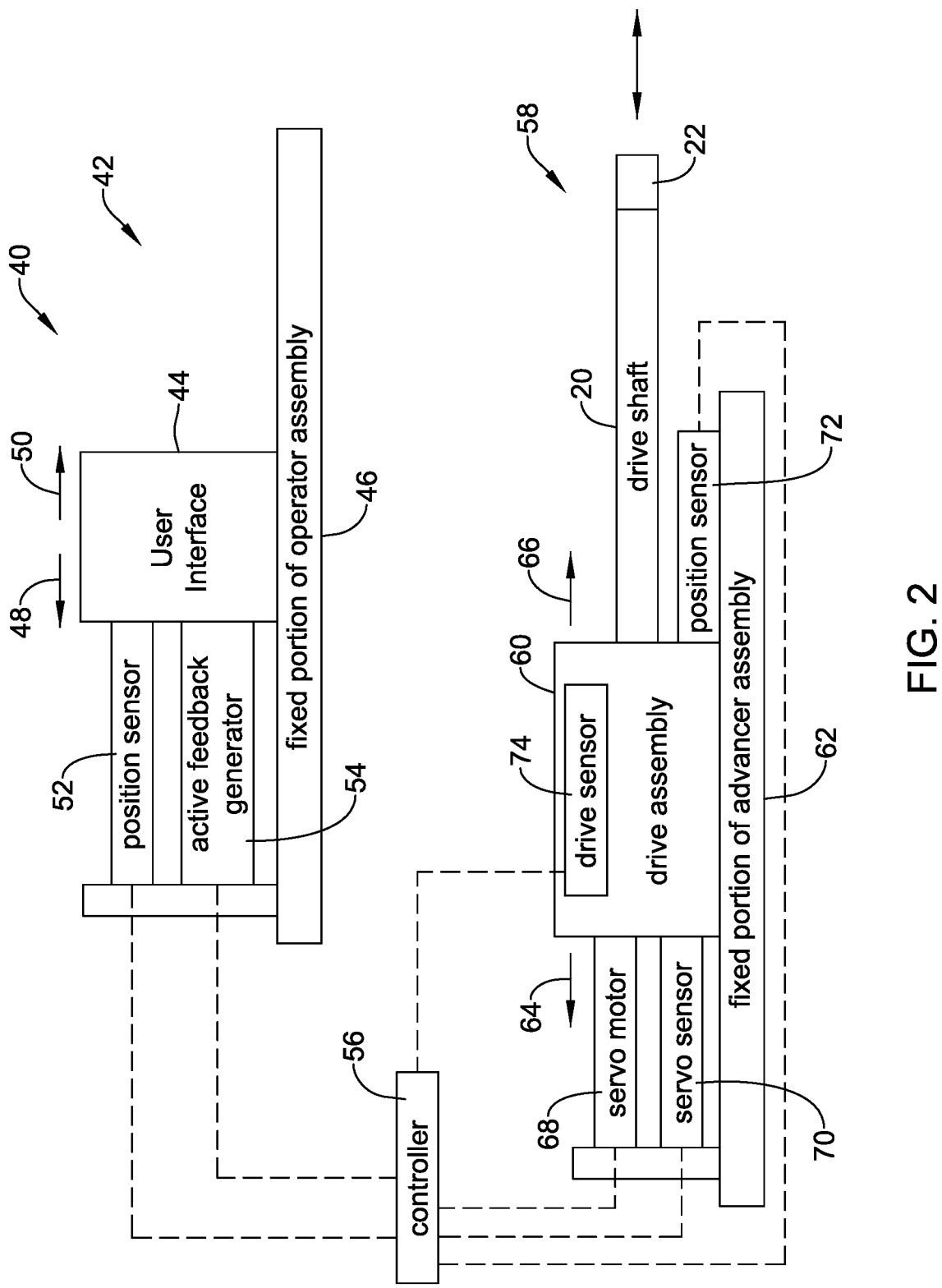
FIG. 2 is a schematic block diagram of an illustrative atherectomy system.

FIG. 2 is a schematic block diagram of an illustrative atherectomy system 40. The illustrative atherectomy system 40 may be considered as being an example of the atherectomy system 10 shown in FIG. 1. The atherectomy system 40 includes an operator assembly 42. The operator assembly 42 may be considered as an example of the operator assembly 24. The operator assembly 42 includes a user interface 44 that may move relative to a fixed portion 46. The user interface 44, which may be a knob, for example, can move back and forth in directions indicated by arrows 48 and 50, respectively.

The operator assembly 42 includes a position sensor 52 and an active feedback generator 54. The position sensor 52 may be adapted to output a signal indicating a current position of the user interface 44. The signal may indicate an actual position. It will be appreciated that by tracking the position of the user interface 44 over time, the velocity of the user interface 44, or how quickly an operator is moving the user interface 44, may be determined. The velocity of the user interface 44 may also be determined by taking a derivative of a function indicating the position of the user interface 44, for example.

The active feedback generator 54 may be adapted to provide feedback to the user interface 44. This may include increasing or decreasing the relative force needed to move the user interface 44 relative to the fixed portion 46. Feedback may include introducing a vibration, for example, as a warning signal to the operator. How the active feedback generator 54 performs, and what feedback is provided when, may be determined by a controller 56.

The active feedback generator 54 may take a variety of forms, as long as the active feedback generator 54 is able to adjust the relative feedback provided by the active feedback generator 54 in response to a received signal. As an example, the active feedback generator 54 may include a ferrofluidic coupler that can operate magnetically. For example, a viscosity of a ferrofluidic fluid passing through an aperture may be varied in response to a received signal. When the viscosity of the fluid increases, a greater resistance to movement of the user interface 44 is felt by the operator, thereby helping the operator to know to apply less force to the interface 44, and thus the lesion, so as to avoid possible situations of the burr sticking or getting stuck. When the viscosity of the fluid decreases, a relatively lesser resistance to motion of the interface 44 is felt by the user.

The active feedback generator 54 may include an electro hydraulic coupler. The electro hydraulic coupler can change the size of an orifice through which a fluid is forced. In some cases, an electro hydraulic coupler may be considered as being a dynamically controllable spring and dashpot system. Changing the orifice dimensions as a response to sensor input can change the compression and rebound rate of the electro hydraulic coupler. Additional details regarding active feedback may be found in U.S. 62/237,679, incorporated by reference herein. The active feedback generator 54 may include an electric motor with a leadscrew, for example.

The position sensor 52 and the active feedback generator 54 are both operably coupled with the controller 56, so that the controller 56 is provided with information regarding the current position of the user interface 44. The controller 56 is also provided with additional information from a variety of sensors that may be included within the atherectomy system 40.

The atherectomy system 40 includes an advancer assembly 58. The advancer assembly 58 includes a drive assembly 60 that is adapted to move relative to a fixed portion 62 of the advancer assembly 58. The drive assembly 60 is adapted to move left and right, in the direction of arrows 64 and 66, respectively, in response to a command signal provided by the controller 56. The advancer assembly 58 includes a servo motor 68 that receives the command signal from the controller 56 and actuates itself to move the drive assembly 60 back and forth in the direction of the arrows 64 and 66. Accordingly, if for example, the operator moved the user interface 44 in the direction indicated by the arrow 50, the servo motor 68 will move the drive assembly 60 in the direction indicated by the arrow 66, or in the anterograde ablation direction. Alternatively, if the operator moves the user interface 44 in the direction indicated by the arrow 48, the servo motor 68 will move the drive assembly 60 in the direction indicated by the arrow 64, or in the retrograde ablation direction. It will be appreciated that by including the servo motor 68 under control of the controller 56, it is possible for the atherectomy system 40 to function in an autonomous ablation mode once the atherectomy burr 22 has reached a particular lesion.

A servo sensor 70 provides the controller 56 with a force signal that indicates the force being applied to the servo motor 68 as a result of resistance to movement of the drive assembly 60. A drive assembly position sensor 72 provides the controller 56 with a drive assembly position signal indicating the current position of the drive assembly 60. A drive motor sensor 74 provides the controller 56 with a drive motor condition signal that indicates a current condition of the drive motor (such as the drive motor 32, not shown in FIG. 2). Examples include motor speed and angular forces being felt by the drive motor.

These sensors can take a variety of forms. For example, position sensors such as the position sensor 52 and the position sensor 72 may include potentiometers, Hall effect sensors, linear variable differential transformers (LVDT), rotary variable differential transformers (RVDT), inductive sensors such as eddy current sensors, proximity sensors and rotary encodes. The servo sensor 70 can include a position sensor or a thermal sensor. The servo sensor 70 may be the servo motor 70 itself, reporting on current and voltage values for the servo motor 70. The drive motor sensor 74 may include a position sensor or a thermal sensor. The drive motor sensor 74 may be the drive motor 32 itself, reporting on current and voltage values for the drive motor 32. Force sensors may include strain gauges, Wheatstone bridges, load cells and force sensitive resistors such as a piezoelectric force sensor.

Figure 3:
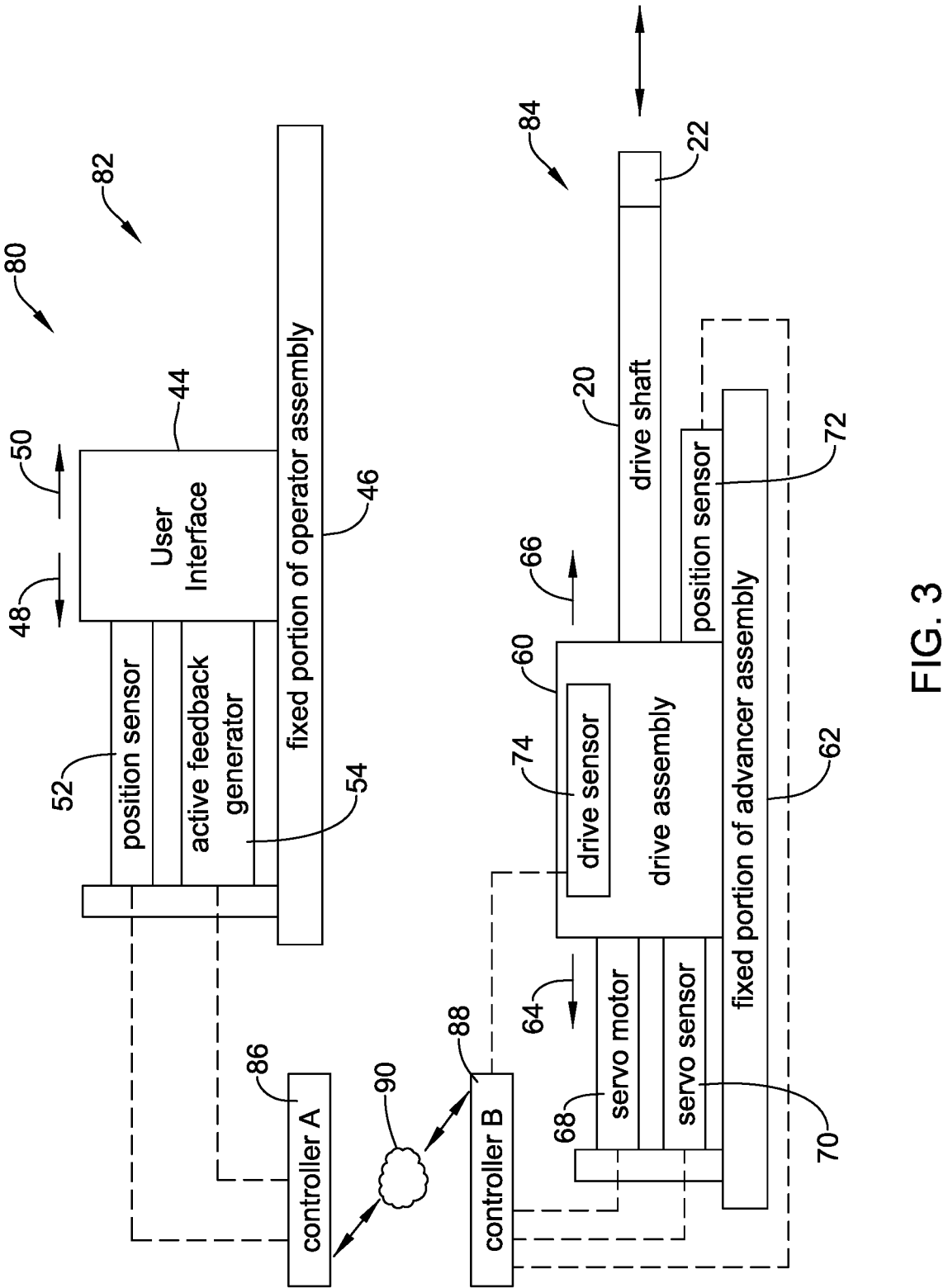
FIG. 3 is a schematic block diagram of an illustrative atherectomy system.

FIG. 3 is a schematic block diagram of an illustrative atherectomy system 80. The illustrative atherectomy system 80 includes an operator assembly 82 and an advancer assembly 84. The atherectomy system 80 is similar to the atherectomy system 40, although the single controller 56 included as part of the atherectomy system 40 is now a first controller 86 that is included as part of the operator assembly 82 and a second controller 88 that is included as part of the advancer assembly 84. The first controller 86 receives a position signal from the position sensor 52 and provides a feedback instruction signal to the active feedback generator 54.

The second controller 88 receives signals from the various sensors 70, 72, 74 and shares this information with the first controller 86. Either the first controller 86 or the second controller 88 determines an appropriate feedback to be generated by the active feedback generator 54. In some cases, the first controller 86 and the second controller 88 are each able to perform all of the functions of the atherectomy system 80 in order to provide redundancy if one of the controllers 86, 88 were to cease functioning or if communication therebetween was lost, even temporarily. In some cases, each of the controllers 86, 88 may include a fail safe mode that allows the atherectomy system 80 to be safely shut down and withdrawn from the patient if there is a failure of one or more components of the atherectomy system 80.

The first controller 86 is in communication with the second controller 88 via a network generically shown as a network 90. In some cases, the operator assembly 82 may be well separated from the advancer assembly 84. This may mean separate rooms in a building, or in separate buildings. The operator assembly 82 and the advancer assembly 84 may be geographically distant from each other. It will be appreciated that by including the servo motor 68 under control of the controller 88 (or the controller 86), it is possible for the atherectomy system 80 to function in an autonomous ablation mode once the atherectomy burr 22 has reached a particular lesion.

Figure 4:
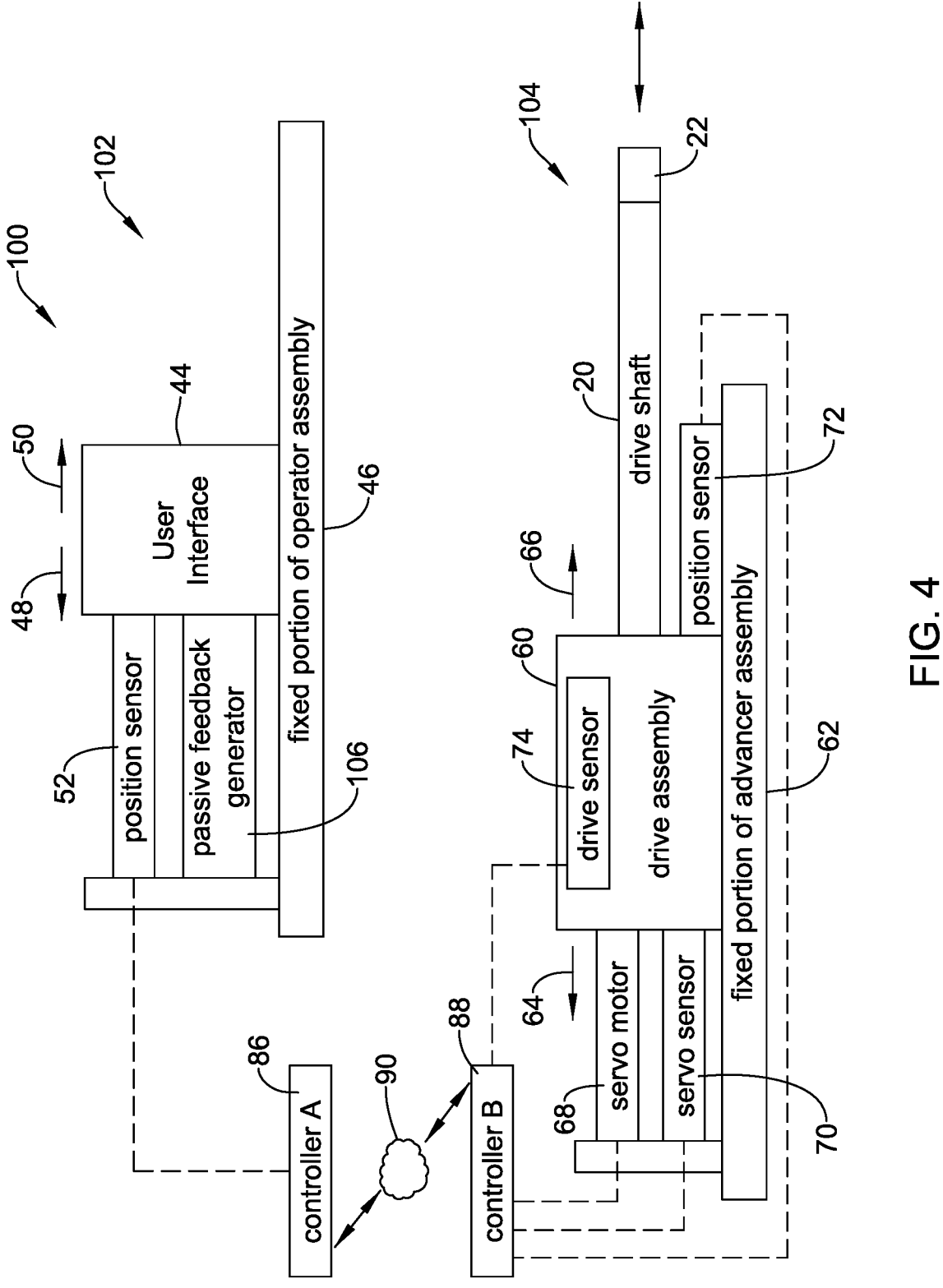
FIG. 4 is a schematic block diagram of an illustrative atherectomy system.

FIG. 4 is a schematic block diagram of an illustrative atherectomy system 100. The illustrative atherectomy system 100 includes an operator assembly 102 and an advancer assembly 104. The operator assembly 102 is similar to the operator assembly 82 shown in FIG. 3, but includes a passive feedback generator 106 in place of the active feedback generator 54. The passive feedback generator 106 does not receive any signals that cause the passive feedback generator 106 to alter its functionality. Rather, the passive feedback generator 106 may include structure that resists changes in motion or applied forces.

As an example, the passive feedback generator 106 may be adapted such that little or no additional resistance or force is generated if the operator is moving the user interface 44 slowly. Alternatively, if the user interface 44 is moved more quickly, the passive feedback generator 106 may provide additional resistance to movement. In some cases, the passive feedback generator 106 may be adapted to provide little or no additional resistance or force if the operator is applying a low force to the user interface 44. However, if the operator applies more force to the user interface 44, the passive feedback generator 106 may apply a greater resistive force in order to limit movement. It will be appreciated that by including the servo motor 68 under control of the controller 88 (or the controller 86), it is possible for the atherectomy system 100 to function in an autonomous ablation mode once the atherectomy burr 22 has reached a particular lesion.

In some cases, the passive feedback generator 106 may include a spring and dashpot. A dashpot is a mechanical device, a damper that resists motion via viscous friction. The resulting force applied by the dashpot may be proportional to velocity, but in the opposite direction. Thus, the dashpot slows the motion. If the user interface 44 is moved slowly, the dashpot will have little impact on applied force. However, if the user interface 44 is moved more quickly, a greater opposing force may be applied. A spring may be included in order to resist displacement. In some cases, a spring and dashpot may function similarly to how a shock absorber functions on a car or truck, for example. In some cases, it is contemplated that a spring and dashpot may include one or more valves or other mechanisms that may cause damping to be different, depending on the direction of movement. In some cases, possible adjustments may include high and low speed compression rate, rebound rate and preload, for example.

In some cases, the passive feedback generator 106 may include a non-Newtonian fluid. A non-Newtonian fluid is a fluid that does not follow Newton's law of viscosity, i.e., constant viscosity independent of stress. In a non-Newtonian fluid, viscosity can change when under force to either be more liquid or more solid. Non-Newtonian fluids may be dilatant, meaning that the viscosity increases when shear is applied (known as shear thickening), or pseudoplastic, in which viscosity decreases with applied shear (known as shear thinning). In some cases, the non-Newtonian fluid includes a dilatant fluid.

In some cases, the passive feedback generator 106 may include a pair of magnets that can be arranged with like poles facing each other. A first magnet may be secured relative to the user interface 44 with a second magnet secured relative to the fixed portion 46. As the two magnets move closer together, there will be an increasing repelling force between the two magnets. As the magnets move away from each other, the repelling force will decrease rapidly. Additional details regarding passive feedback may be found in U.S. 62/237,679, incorporated by reference herein.

Figure 5:
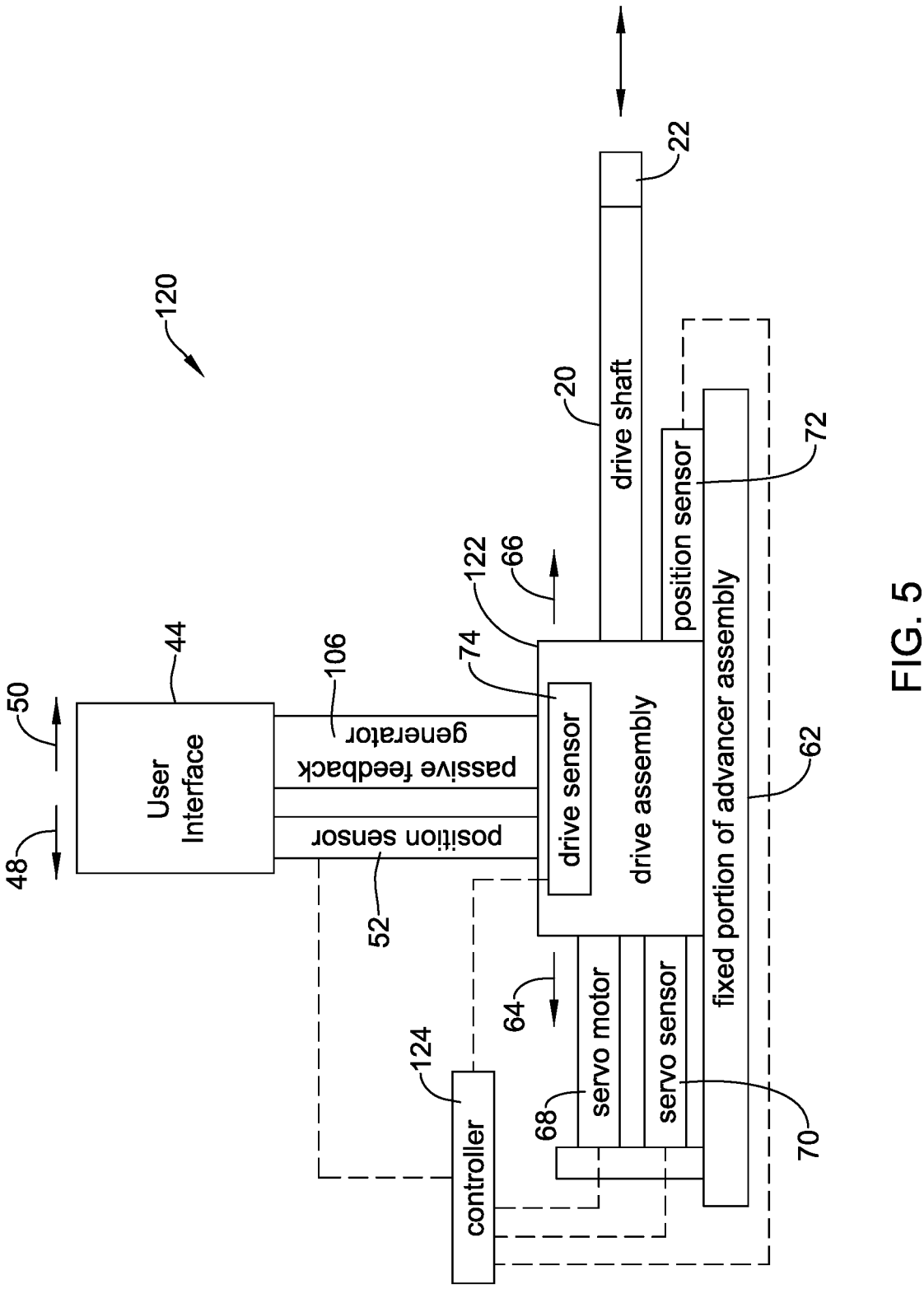
FIG. 5 is a schematic block diagram of an illustrative atherectomy system.

FIG. 5 is a schematic block diagram of an illustrative atherectomy system 120 that combines local control with passive feedback. As shown, the passive feedback generator 106 is positioned between the user interface 44 and a drive assembly 122. In some instances, this arrangement may be lower cost, as only one actuator and one controller is needed. In some cases, this arrangement may be designed with a mechanical fail-safe instead of a more complicated electrical fail-safe. A controller 124 receives a position signal from the position sensor 52, which indicates a desired travel, and determines an appropriate command signal for the servo motor 68. The controller 124 also receives signals form the servo motor sensor 70, the drive motor sensor 74 and the position sensor 72. The servo motor 68 moves the drive assembly 122 in accordance with the command signal from the controller 124. It will be appreciated that by including the servo motor 68 under control of the controller 124, it is possible for the atherectomy system 120 to function in an autonomous ablation mode once the atherectomy burr 22 has reached a particular lesion.

Figure 6:
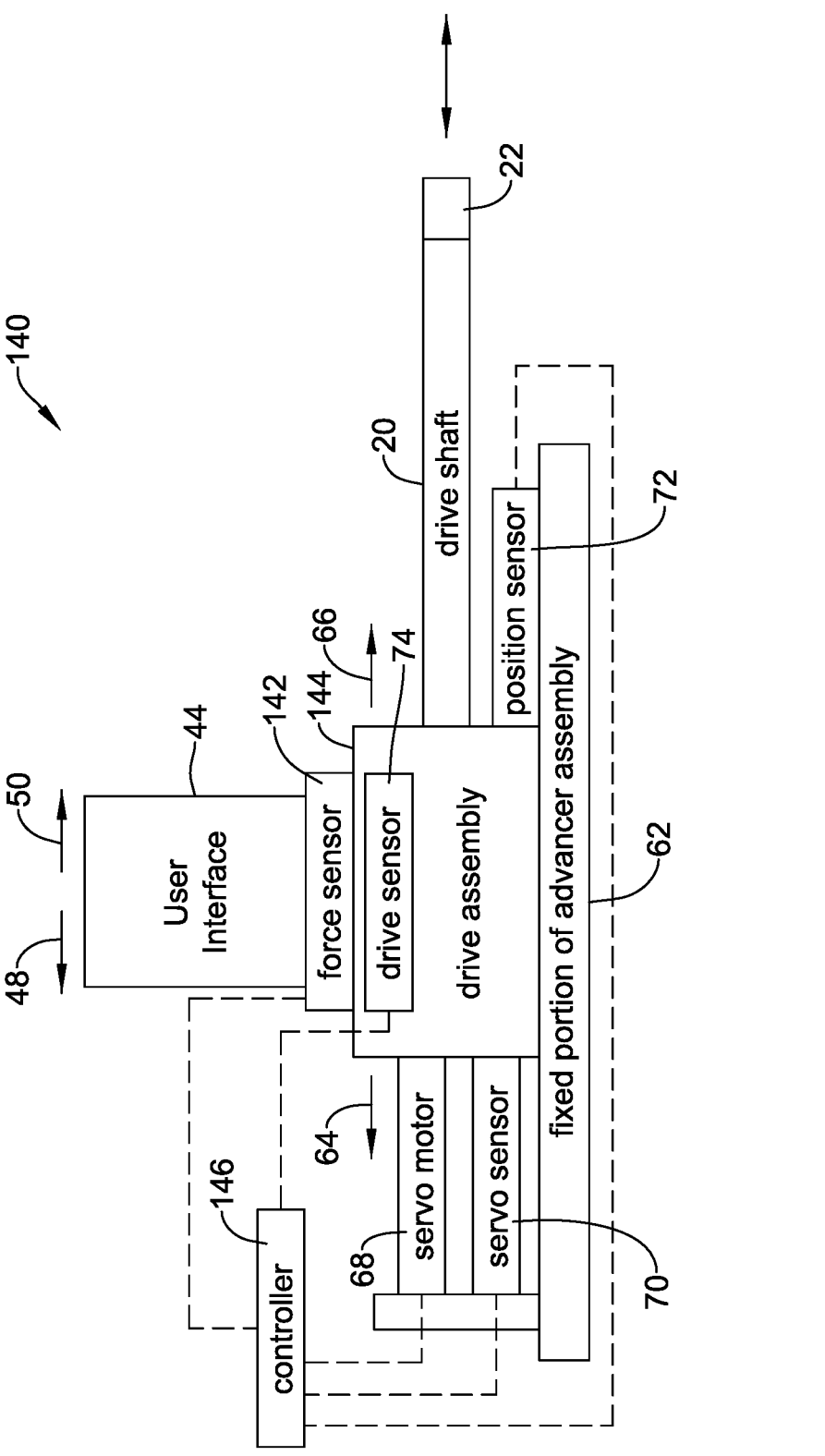
FIG. 6 is a schematic block diagram of an illustrative atherectomy system.

FIG. 6 is a schematic block diagram of an illustrative atherectomy system 140 that provides augmented direct control. A force sensor 142 is disposed between the user interface 44 and a drive assembly 144. In some cases, the servo motor 68 is able to provide feedback to the user in the form of resisting movement of the user interface 44. For example, the servo sensor 70 may sense that the burr 22 is nearing a stall condition as the user is applying force to the user interface 44. The servo motor 68 being able to overpower the user does not allow the drive assembly 144 to translate, as allowing the drive assembly 144 to translate could cause a stall, but rather applies motion to prevent stall. This force would be felt directly by the user through the user interface 44. A controller 146 receives a force signal from the force sensor 142. The controller 146 also receives signals form the servo motor sensor 70, the drive motor sensor 74 and the position sensor 72. The servo motor 68 moves the drive assembly 144 in accordance with the command signal from the controller 146. This arrangement leads to an inexpensive configuration with a very simply fail safe mechanism. This means that a surgeon can continue with a case with reduced capacity, even in the event of a failure. It will be appreciated that by including the servo motor 68 under control of the controller 146, it is possible for the atherectomy system 140 to function in an autonomous ablation mode once the atherectomy burr 22 has reached a particular lesion.

Figure 7:
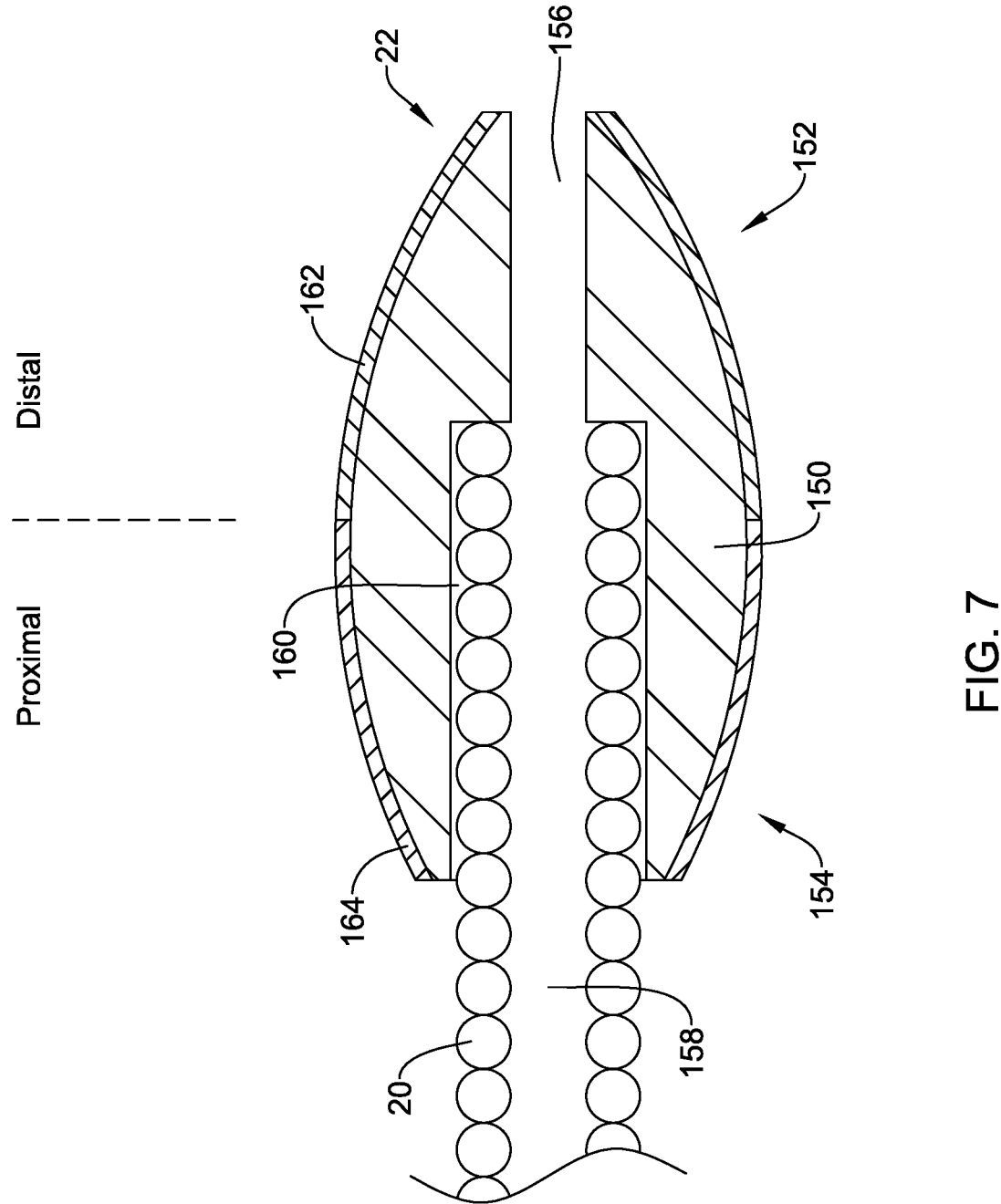
FIG. 7 is a cross-sectional view of an illustrative atherectomy burr.

FIG. 7 is a partial cross-sectional view of the atherectomy burr 22 that is adapted for performing both anterograde ablation and retrograde ablation. The atherectomy burr 22 may be seen as having an ovoid body 150 including a distal tapered portion 152 and a proximal tapered portion 154. The atherectomy burr 22 includes a lumen 156 that aligns with a corresponding lumen 158 extending through the drive shaft 20 in order to accommodate a guidewire (not shown). The atherectomy burr 22 includes a void 160 that is adapted to accommodate the drive shaft 20 and to secure the atherectomy burr 22 relative to the drive shaft 20. The atherectomy burr 22 may be adhesively secured, for example, or may be welded or soldered into place. An abrasive material 162, such as but not limited to diamonds, may be disposed over the distal tapered portion 152. An abrasive material 164, such as but not limited to diamonds, may be disposed over the proximal tapered portion 154. Accordingly, the atherectomy burr 22 may be considered as being adapted for both anterograde ablation and retrograde ablation.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An atherectomy system, comprising:
an advancer assembly;
a drive assembly adapted to translate relative to the advancer assembly, the drive assembly including:
   a rotatable drive shaft operably coupled with the drive assembly such that the rotatable drive shaft translates with the drive assembly; and
   an atherectomy burr coupled to the drive shaft, the drive shaft adapted to rotate the atherectomy burr at speeds exceeding 100,000 revolutions per minute;
   wherein the drive shaft and the atherectomy burr are adapted to be advanced through a patient's vasculature to reach a treatment site within the patient's vasculature;
an operator assembly including a user interface that an operator engages with in order to indicate requested translation of the drive assembly, the user interface configured to output a request signal indicating requested translation of the drive assembly;
one or more sensors adapted to ascertain one or more conditions of the drive assembly and to output one or more condition signals;
a controller operably coupled with the operator assembly and the drive assembly, the controller adapted to:
   receive the request signal from the operator assembly and the one or more condition signals;
   determine a command signal in response to the received request signal and the received one or more condition signals; and
   provide the command signal to the drive assembly;
   wherein the drive assembly is adapted to translate relative to the advancer assembly in accordance with the command signal.

2. The atherectomy system of claim 1, further comprising a servo motor that is adapted to translate the drive assembly relative to the advancer assembly in response to the command signal.

3. The atherectomy system of claim 2, wherein one of the one or more sensors comprises a servo force sensor that is adapted to provide the controller with a force signal indicating resistance to translation of the drive assembly relative to the advancer assembly.

4. The atherectomy system of claim 2, wherein the drive assembly further comprises a drive motor adapted to rotate the rotatable drive shaft.

5. The atherectomy system of claim 4, wherein one of the one or more sensors comprises a drive motor sensor that is adapted to provide the controller with a drive motor condition signal indicating a current operating condition of the drive motor.

6. The atherectomy system of claim 2, wherein one of the one or more sensors comprises a drive assembly position sensor that is adapted to provide the controller with a drive assembly position signal indicating a relative position of the drive assembly.

7. The atherectomy system of claim 2, further comprising a feedback generator that is adapted to change a feel of the user interface in order to indicate a sensed condition of the drive assembly.

8. The atherectomy system of claim 7, wherein the feedback generator comprises an active feedback generator.

9. The atherectomy system of claim 8, wherein the controller is further adapted to:
determine an active feedback generation signal based upon signals received from the one or more sensors adapted to ascertain one or more conditions of the drive assembly; and
provide the active feedback generation signal to the active feedback generator;
wherein the active feedback generator is adapted to generate feedback to the user interface in accordance with the active feedback generation signal.

10. The atherectomy system of claim 9, wherein the controller is further adapted to:
determine the active feedback generation signal in accordance with a first set of tuning parameter values when the operator is requesting that the drive assembly move in an anterograde ablation direction; and
determine the active feedback generation signal in accordance with a second set of tuning parameter values, different from the first set of tuning parameter values, when the operator is requesting that the drive assembly move in a retrograde ablation direction.

11. The atherectomy system of claim 10, wherein the controller is further adapted to provide a first level of feedback to the user interface via the active feedback generator when the operator is requesting low force movement of the drive assembly and to provide a greater level of feedback to the user interface via the active feedback generator when the operator is requesting high force movement of the drive assembly.

12. The atherectomy system of claim 10, wherein the controller is further adapted to provide a first level of feedback to the user interface via the active feedback generator when the operator is requesting that the drive assembly move in the anterograde ablation direction and to provide a greater level of feedback to the user interface via the active feedback generator when the operator is requesting that the drive assembly move in the retrograde ablation direction.

13. The atherectomy system of claim 1, wherein the atherectomy burr includes:
a tapered body including a proximal taper and a distal taper;
a first ablating surface disposed on the proximal taper for retrograde ablation; and
a second ablating surface disposed on the distal taper for anterograde ablation.

14. The atherectomy system of claim 1, wherein the controller is further adapted to engage a fail-safe operation in the event that communication between the controller and any of the one or more sensors is lost.

15. The atherectomy system of claim 1, wherein the operator assembly further comprises a user interface position sensor that provides the controller with a signal indicating a current position of the user interface.

16. An atherectomy system that is adapted for both anterograde direction ablation and retrograde direction ablation, the atherectomy system comprising:
an operator assembly including:
a user interface that an operator engages with in order to indicate requested translation of a drive assembly, the user interface configured to output a request signal indicating requested translation of the drive assembly;
a first controller operably coupled with the operator assembly and adapted to receive the request signal from the user interface; and
an advancer assembly including:
a drive assembly adapted to translate relative to the advancer assembly, the drive assembly including:
a drive shaft operably coupled with the drive assembly such that the drive shaft translates with the drive assembly;
a drive motor adapted to rotate the drive shaft at atherectomy speeds; and
an atherectomy burr coupled to the drive shaft;
one or more sensors adapted to ascertain one or more conditions of the drive assembly and to output one or more condition signals;
a second controller operably coupled with the operator assembly and the drive assembly, the second controller adapted to:
receive the request signal from the first controller and the one or more condition signals;
determine a command signal in response to the received request signal and the received one or more condition signals; and
provide the command signal to the drive assembly;
wherein the drive assembly is adapted to translate relative to the advancer assembly in accordance with the command signal.

17. The atherectomy system of claim 16, wherein the first controller and the second controller are each adapted to communicate wirelessly with each other.

18. The atherectomy system of claim 16, wherein the operator assembly further comprises an active feedback generator operably coupled with the user interface.

19. The atherectomy system of claim 16, wherein the atherectomy burr includes:
a tapered body including a proximal taper and a distal taper;
a first ablating surface disposed on the proximal taper for retrograde ablation; and
a second ablating surface disposed on the distal taper for anterograde ablation.

20. An atherectomy system, comprising:
an advancer assembly;
a drive assembly adapted to translate relative to the advancer assembly, the drive assembly including:
a drive shaft operably coupled with the drive assembly such that the drive shaft translates with the drive assembly;
a drive motor adapted to rotate the drive shaft at atherectomy speeds; and
an atherectomy burr coupled to the drive shaft;
an operator assembly including:
a user interface that an operator engages with in order to indicate requested translation of the drive assembly, the user interface configured to output a request signal indicating requested translation of the drive assembly;
an active feedback generator operably coupled with the user interface, the active feedback generator adapted to alter a feel of the user interface in response to a received feedback signal;
one or more sensors adapted to ascertain one or more conditions of the drive assembly and to output one or more condition signals;
a controller operably coupled with the operator assembly and the drive assembly, the controller adapted to:
receive the request signal from the operator assembly and the one or more condition signals;
determine a command signal in response to the received request signal and the received one or more condition signals;
determine the feedback signal;
provide the command signal to the drive assembly; and
provide the feedback signal to the active feedback generator;
wherein the drive assembly is adapted to translate relative to the advancer assembly in accordance with the command signal.

* * * * *